(12) United States Patent
Tyler et al.

(10) Patent No.: US 9,579,343 B2
(45) Date of Patent: *Feb. 28, 2017

(54) DIRECT COMPRESSION POLYMER TABLET CORE

(71) Applicant: Genzyme Corporation, Cambridge, MA (US)

(72) Inventors: Joseph Tyler, Somerville, MA (US); John S. Petersen, Acton, MA (US)

(73) Assignee: GENZYME CORPORATION, Cambridge, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/481,071

(22) Filed: Sep. 9, 2014

(65) Prior Publication Data

US 2015/0056278 A1 Feb. 26, 2015

Related U.S. Application Data

(63) Continuation of application No. 13/467,448, filed on May 9, 2012, now abandoned, which is a continuation of application No. 12/461,143, filed on Aug. 3, 2009, now Pat. No. 8,187,631, which is a continuation of application No. 11/196,799, filed on Aug. 3, 2005, now abandoned, which is a continuation of application No. 10/785,322, filed on Feb. 24, 2004, now abandoned, which is a continuation of application No. 09/691,429, filed on Oct. 18, 2000, now Pat. No. 6,733,780.

(60) Provisional application No. 60/174,227, filed on Jan. 3, 2000, provisional application No. 60/160,258, filed on Oct. 19, 1999.

(51) Int. Cl.
*A61K 9/28* (2006.01)
*A61K 31/785* (2006.01)
*A61K 9/20* (2006.01)

(52) U.S. Cl.
CPC .......... *A61K 31/785* (2013.01); *A61K 9/2009* (2013.01); *A61K 9/2013* (2013.01); *A61K 9/2027* (2013.01); *A61K 9/28* (2013.01); *A61K 9/282* (2013.01); *A61K 9/2866* (2013.01)

(58) Field of Classification Search
None
See application file for complete search history.

(56) References Cited

U.S. PATENT DOCUMENTS

| | | | |
|---|---|---|---|
| 2,426,125 A | 8/1947 | Steiner | |
| 2,456,428 A | 12/1948 | Parker | |
| 2,463,824 A | 3/1949 | Steiner et al. | |
| 3,104,205 A | 9/1963 | Hainer et al. | |
| 3,308,020 A | 3/1967 | Tennant et al. | |
| 3,332,841 A | 7/1967 | Ainsworth et al. | |
| 3,383,236 A | 5/1968 | Brindamour | |
| 3,431,138 A | 3/1969 | Zingerman et al. | |
| 3,539,380 A | 11/1970 | Johnson et al. | |
| 3,624,209 A | 11/1971 | Granatek et al. | |
| 3,980,770 A | 9/1976 | Ingelman et al. | |
| 4,016,209 A | 4/1977 | Wagner et al. | |
| 4,071,478 A | 1/1978 | Shen et al. | |
| 4,115,537 A | 9/1978 | Driscoll et al. | |
| 4,143,130 A | 3/1979 | Imondi et al. | |
| 4,172,120 A | 10/1979 | Todd et al. | |
| 4,181,718 A | 1/1980 | Mason et al. | |
| 4,183,918 A | 1/1980 | Asher et al. | |
| 4,205,064 A | 5/1980 | Wagner et al. | |
| 4,211,763 A | 7/1980 | Marshall et al. | |
| 4,247,393 A | 1/1981 | Wallace | |
| 4,264,573 A | 4/1981 | Powell et al. | |
| 4,302,440 A | 11/1981 | John et al. | |
| 4,341,563 A | 7/1982 | Kurihara et al. | |
| 4,344,993 A | 8/1982 | Schmidt et al. | |

(Continued)

FOREIGN PATENT DOCUMENTS

AU 689797 4/1998
CH 656 535 A5 7/1986

(Continued)

OTHER PUBLICATIONS

Burt, Helen et al., "Ion-Exchange Resins as Potential Phosphate-Binding Agents for Renal Failure Patients: Effect of the Physiochemical Properties of Resins on Phosphate and Bile Salt Binding," *Journal of Pharmaceutical Sciences*, vol. 76, No. 5 (May 1987) pp. 379-383.

(Continued)

*Primary Examiner* — Michael G Hartley
*Assistant Examiner* — Nabila Ebrahim
(74) *Attorney, Agent, or Firm* — Jones Day

(57) ABSTRACT

The present invention provides a tablet core which comprises at least about 95% by weight of an aliphatic amine polymer. The invention also provides a method of producing a tablet core comprising at least about 95% by weight of an aliphatic amine polymer resin The method comprises the step of compressing the aliphatic amine polymer to form the tablet core. The tablet core can further include one or more excipients. In this embodiment, the method of producing the tablet core comprises the steps of: (1) hydrating the aliphatic amine polymer to the desired moisture level; (2) blending the aliphatic amine polymer with the excipients in amounts such that the polymer comprises at least about 95% by weight of the resulting blend; and (3) compressing the blend to form the tablet core. The present invention further relates to a coated tablet comprising an aliphatic amine polymer core wherein the coating is a water based coating.

20 Claims, 1 Drawing Sheet

(56) References Cited

U.S. PATENT DOCUMENTS

| | | |
|---|---|---|
| 4,439,419 A | 3/1984 | Vecchio |
| 4,504,640 A | 3/1985 | Harada et al. |
| 4,507,466 A | 3/1985 | Tomalia et al. |
| 4,518,433 A | 5/1985 | McGinley et al. |
| 4,528,184 A | 7/1985 | Kurono et al. |
| 4,539,198 A | 9/1985 | Powell et al. |
| 4,543,370 A | 9/1985 | Porter et al. |
| 4,605,701 A | 8/1986 | Harada et al. |
| 4,631,305 A | 12/1986 | Guyer et al. |
| 4,762,524 A | 8/1988 | Chambers et al. |
| 4,849,227 A | 7/1989 | Cho |
| 4,853,437 A | 8/1989 | Lukach et al. |
| 4,871,779 A | 10/1989 | Killat et al. |
| 4,895,621 A | 1/1990 | Hassler |
| 4,956,182 A | 9/1990 | Bequette et al. |
| 4,983,398 A | 1/1991 | Gaylord et al. |
| 4,983,399 A | 1/1991 | Maish |
| 5,053,423 A | 10/1991 | Liu |
| 5,055,197 A | 10/1991 | Albright et al. |
| 5,073,380 A | 12/1991 | Babu et al. |
| 5,108,767 A | 4/1992 | Mulchandani et al. |
| 5,194,464 A | 3/1993 | Itoh et al. |
| 5,262,167 A | 11/1993 | Vegesna et al. |
| 5,302,531 A | 4/1994 | Bauer |
| 5,373,052 A | 12/1994 | Fukuda et al. |
| 5,374,422 A | 12/1994 | St. Pierre et al. |
| 5,376,396 A | 12/1994 | Clark |
| 5,401,515 A | 3/1995 | Woodard et al. |
| 5,414,068 A | 5/1995 | Bliem et al. |
| 5,428,112 A | 6/1995 | Ahlers et al. |
| 5,430,110 A | 7/1995 | Ahlers et al. |
| 5,447,726 A | 9/1995 | Nomura |
| 5,455,047 A | 10/1995 | Bequette et al. |
| 5,462,730 A | 10/1995 | McTaggart et al. |
| 5,487,888 A | 1/1996 | Mandeville et al. |
| 5,496,545 A | 3/1996 | Holmes-Farley et al. |
| 5,520,932 A | 5/1996 | McCurdy et al. |
| 5,530,092 A | 6/1996 | Meijer et al. |
| 5,561,214 A | 10/1996 | Yeske et al. |
| 5,607,669 A | 3/1997 | Mandeville, III et al. |
| 5,610,268 A | 3/1997 | Meijer et al. |
| 5,618,530 A | 4/1997 | Mandeville, III et al. |
| 5,624,963 A | 4/1997 | Mandeville, III et al. |
| 5,654,003 A | 8/1997 | Fuisz et al. |
| 5,667,775 A | 9/1997 | Holmes-Farley et al. |
| 5,679,717 A | 10/1997 | Mandeville, III et al. |
| 5,686,106 A | 11/1997 | Kelm et al. |
| 5,693,675 A | 12/1997 | Mandeville, III et al. |
| 5,702,696 A | 12/1997 | Mandeville, III et al. |
| 5,703,188 A | 12/1997 | Mandeville, III et al. |
| 5,709,880 A | 1/1998 | Del Corral et al. |
| 5,718,920 A | 2/1998 | Notenbomber |
| 5,747,067 A | 5/1998 | Auguello et al. |
| 5,750,148 A | 5/1998 | Maruyama et al. |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville, III et al. |
| 5,900,475 A | 5/1999 | Mandeville, III et al. |
| 5,919,832 A | 7/1999 | Mandeville, III et al. |
| 5,959,069 A | 9/1999 | Gluck et al. |
| 5,969,090 A | 10/1999 | Mandeville, III et al. |
| 5,985,938 A | 11/1999 | Holmes-Farley et al. |
| 6,022,533 A | 2/2000 | Goto et al. |
| 6,034,129 A | 3/2000 | Mandeville, III et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Pillay et al. |
| 6,149,938 A | 11/2000 | Bonadeao et al. |
| 6,177,478 B1 | 1/2001 | Holmes-Farley et al. |
| 6,180,754 B1 | 1/2001 | Stutts et al. |
| 6,187,897 B1 | 2/2001 | Kawashima et al. |
| 6,190,650 B1 | 2/2001 | Matthews et al. |
| 6,203,785 B1 | 3/2001 | Holmes-Farley et al. |
| 6,248,318 B1 | 6/2001 | Huval et al. |
| 6,264,937 B1 | 7/2001 | Mandeville et al. |
| 6,274,713 B1 | 8/2001 | Sieving et al. |
| 6,281,252 B1 | 8/2001 | Holmes-Farley et al. |
| 6,284,275 B1 | 9/2001 | Chen |
| 6,335,402 B1 | 1/2002 | Mihan et al. |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville, III et al. |
| 7,220,406 B2 | 5/2007 | Burke |
| 7,335,795 B2 | 2/2008 | Chang et al. |
| 7,342,083 B2 | 3/2008 | Chang et al. |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 7,638,524 B2 | 12/2009 | Huval et al. |
| 7,985,418 B2 | 7/2011 | Bhagat et al. |
| 8,808,738 B2 | 8/2014 | Bhagat et al. |
| 9,095,509 B2 | 8/2015 | Bhagat et al. |
| 2002/0054903 A1 | 5/2002 | Tyler et al. |
| 2002/0114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0003113 A1 | 1/2003 | Lewandowski |
| 2003/0039627 A1 | 2/2003 | Holmes-Farley et al. |
| 2003/0049226 A1 | 3/2003 | Burke et al. |
| 2003/0086898 A1 | 5/2003 | Holmes-Farley et al. |
| 2003/0133902 A1 | 7/2003 | Holmes-Farley et al. |
| 2003/0161875 A1 | 8/2003 | Murpani et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2003/0215585 A1 | 11/2003 | Bunick |
| 2004/0019020 A1 | 1/2004 | Jozefiak et al. |
| 2004/0022844 A1 | 2/2004 | Hasenzahl et al. |
| 2004/0120922 A1 | 6/2004 | Burke |
| 2004/0166156 A1 | 8/2004 | Tyler et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville, III et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |

(56) References Cited

U.S. PATENT DOCUMENTS

| | | |
|---|---|---|
| 2006/0024336 A1 | 2/2006 | Charmot et al. |
| 2006/0024368 A1 | 2/2006 | Fassihi et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0116391 A1 | 6/2006 | Horbury et al. |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville, III et al. |
| 2007/0190135 A1 | 8/2007 | Matsuda et al. |
| 2007/0224283 A1 | 9/2007 | Chang et al. |
| 2008/0014288 A1 | 1/2008 | Huval et al. |
| 2008/0107737 A1 | 5/2008 | Chang et al. |
| 2008/0226735 A1 | 9/2008 | Moerck et al. |
| 2008/0292697 A1 | 11/2008 | Tyler et al. |
| 2008/0299199 A1 | 12/2008 | Bar-Shalom et al. |
| 2015/0104510 A1 | 4/2015 | Bhagat et al. |
| 2016/0113961 A1 | 4/2016 | Bhagat et al. |

FOREIGN PATENT DOCUMENTS

| | | |
|---|---|---|
| CN | 1290515 | 12/2006 |
| DE | 4010271 | 10/1991 |
| EP | 0162388 A1 | 11/1985 |
| EP | 0375350 A2 | 6/1990 |
| EP | 0379161 A2 | 7/1990 |
| EP | 0449151 A2 | 10/1991 |
| EP | 0534304 A1 | 3/1993 |
| EP | 0605757 A1 | 7/1994 |
| EP | 0737759 | 10/1996 |
| EP | 0997148 | 5/2000 |
| EP | 1153940 | 11/2001 |
| EP | 1210935 | 6/2002 |
| EP | 1304104 | 4/2003 |
| EP | 0211991 | 3/2007 |
| FR | 2217010 A | 9/1974 |
| FR | 2232563 | 1/1975 |
| GB | 929391 | 6/1963 |
| GB | 1238597 A | 7/1971 |
| GB | 1470538 | 4/1977 |
| GB | 2036048 A | 11/1978 |
| GB | 2391730 | 12/1978 |
| GB | 1573487 | 8/1980 |
| GB | 2090605 | 7/1982 |
| GB | 2276170 | 9/1994 |
| GB | 2169356 | 7/2000 |
| JP | 50-34095 | 2/1975 |
| JP | 58079022 | 5/1983 |
| JP | 60152424 A | 8/1985 |
| JP | 62-132830 | 6/1987 |
| JP | 4-503962 | 3/1990 |
| JP | 5-244915 | 9/1993 |
| JP | 6-321786 | 11/1994 |
| JP | 10-330269 | 12/1998 |
| JP | 10316576 A | 12/1998 |
| JP | 2000178182 A | 6/2000 |
| JP | 2006-008637 | 1/2006 |
| NL | 7401543 | 8/1974 |
| NL | 7603653 | 10/1976 |
| RU | 1808015 A3 | 4/1993 |
| WO | WO 90/02148 | 3/1990 |
| WO | WO 92/10522 | 6/1992 |
| WO | WO 93/00915 | 1/1993 |
| WO | WO 93/05793 | 1/1993 |
| WO | WO 94/19379 | 1/1994 |
| WO | WO 94/04596 | 3/1994 |
| WO | WO 94/27620 | 12/1994 |
| WO | WO 94/27621 | 12/1994 |
| WO | WO 95/05184 | 2/1995 |
| WO | WO 96/21454 | 7/1996 |
| WO | WO 96/25440 | 8/1996 |
| WO | WO 97/49771 | 12/1997 |
| WO | WO 98/42355 | 10/1998 |
| WO | WO 98/44933 | 10/1998 |
| WO | WO 99/22721 | 5/1999 |
| WO | WO 00/22008 | 4/2000 |
| WO | WO 02/085378 | 10/2002 |
| WO | WO 2004/099288 | 11/2004 |
| WO | WO 2005/021000 | 3/2005 |
| WO | WO 2005/041902 | 5/2005 |
| WO | WO 2005/065291 | 7/2005 |
| WO | WO 2005/072752 | 8/2005 |
| WO | WO 2006/022759 | 3/2006 |
| WO | WO 2006/050314 | 5/2006 |
| WO | WO 2006/050315 | 5/2006 |
| WO | WO 2007/035313 | 3/2007 |

OTHER PUBLICATIONS

C and C, Product Catalog, Manesty B3B Rotary Tablet Presses (Product# manesty-b3b-16) downloaded online, Mar. 5, 2014.

Delmez, James A. et al., "Hyperphosphatemia: Its Consequences and Treatment in Patients with Chronic Renal Disease," *American Journal of Kidney Diseases*, vol. XIX, No. 4 (1992) pp. 303-317.

Emmett, Michael et al., "Calcium Acetate Control of Serum Phosphorus in Hemodialysis Patients," *American Journal of Kidney Diseases*, vol. XVII, No. 5 (1991) pp. 544-550.

Ghosh, J.P. et al., "Preparation and Properties of a New Chelating Resin Containing 2-Nitroso-1-naphthol," *Talanta*, vol. 28 (1981) pp. 957-959.

Mai, Martin L. et al., "Calcium acetate, an effective phosphorus binder in patients with renal failure," *Kidney International*, vol. 36 (1989) pp. 690-695.

McGary, T.J. et al., "Polycation as an Alternative Osmotic Agent and Phosphate Binder in Peritoneal Dialysis," *Uremia Investigation*, vol. 8, No. 2 (1984-85) pp. 79-84.

Munson, Paul L., "Studies on the Role of the Parathyroids in Calcium and Phosphorus Metabolism," *Annals New York Academy of Sciences* (Jun. 1993) pp. 776-795.

Petrariu, I. et al., "Hofmann degradation in quaternary basic ammonium polymers: I. Degradation of the linear and crosslined basic benzylic polyelectrolytes in alkaline media," *Majer. Plast.* (Bucharest), vol. 9, No. 9 (1972) pp. 467-472.

Physicians' Desk Reference, Consult 1992 Supplements for Revisions—"PhosLo® Calcium Acetate Tablets".

Physicians' Desk Reference, Consult 1992 Supplements for Revisions—"Amphojel® Suspension Tablets", p. 2429.

Proceedings of the American Chemical Society Division of Polymeric Materials: Science and Engineering, Boston, Massachusetts, vol. 62 (1990) pp. 259-263.

Salusky, I.B. et al., "Aluminum Accumulation During Treatment with Aluminum Hydroxide and Dialysis in Children and Young Adults with Chronic Renal Disease," *The New England Journal of Medicine*, vol. 324, No. 8 (1991) pp. 527-531.

Shkinev, V.M. et al., "Anion exchange extraction and enrichment from aqueous solutions by quaternary ammonium reagents," *Solvent Extraction and Ion Exchange*, vol. 7, No. 3 (1989) pp. 499-510.

Slatopolsky, Eduardo et al., "Calcium Carbonate as a Phosphate Binder in Patients with Chronic Renal Failure Undergoing Dialysis," *The New England Journal of Medicine*, vol. 315, No. 3 (1986) pp. 157-161.

Ullmanns Encyklopädie der technischen Chemie—Band 19: *Polyolefine* (1980) pp. 167-178.

Warshawsky, A., "Ion Exchange and Sorption Processes in Hydrometallurgy", Critical Reports on Applied Chemistry, vol. 19:

(56) References Cited

OTHER PUBLICATIONS

*Chapter 4: Chelating Ion Exchangers*, M. Streat & D. Naden (Eds.), John Wiley & Sons (1987) pp. 166-225.
Winston, Anthony and Kirchner, Darrell, "Hydroxamic Acid Polymers. Effect of Structure of the Selective Chelation of Iron in Water," *Macromolecules*, vol. 11, No. 3 (1978) pp. 597-603.
Winston, Anthony and McLaughline, Glenn R., "Hydroxamic Acid Polymers. II. Design of a Polymeric Chelating Agent for Iron," *Journal of Polymer Science*, vol. 14 (1976) pp. 2155-2165.
Zabutaya, F.I., et al., "Proton NMR spectroscopic study of the reaction of epichlorahydrin with allyamine," *Uzb. Chim. Zh.*, vol. 3 (1984) pp. 23-27. (English Abstract, see XP 002025287).
International Search Report dated Apr. 12, 2007 for PCT/US2006/035370.
Examination Report dated Jan. 20, 2011 for Australian Application No. 2006292672.
Examination Report dated Nov. 8, 2010 for Japanese Application No. 2001-531357.
Examination Report dated Sep. 29, 2010 for Brazilian Application No. PI 0015061-4.
Bhadra, D. et al., "Glycodendrimeric Nanoparticulate Carriers of Primaquine Phosphate for Liver Targeting" International Journal of Pharmaceutics, 295 (Mar. 2005) 221-233.
Caramella, Carla et al. "Experimental Evidence of Disintegration Mechanisms" Acta Pharm. Technol., 35:1 (1989) 30-33.
Chertow, Glenn M. et al. "The Effects of Sevelamer and Calcium Acetate on Proxies of Atherosclerotic and Arteriosclerotic Vascular Disease in Hemodialysis Patients" Am. J. Nephrol., 23:5 (2003) 307-314.
De Brabander-Van Den Berg, Ellen M. M. et al., "Poly(propylenimin)-Dendrimere: Synthese in größerem Maβstab durch heterogen katalysierte Hydrierungen" Angew. Chem. (1993) 1370-1372. [in German only].
Duncan, Ruth et al., "Dendrimer biocompatibility and toxicity" Advanced Drug Delivery Reviews, 57 (2005) 2215-2237.
Ferrari, F. et al. "Investigation on Bonding and Distintegration Properties of Pharmaceutical Materials" International Journal of Pharmaceutics, 136 (1996) 71-79.
Gao, C., "Hyperbranched polymers made from A2, B2 and BB'2 type monomers, 2. Preparation of hyperbranched copoly(sulfone-amine)s by polyaddition of N-ethylethylenediamine and piperazine to divinylsulfone" Polymer (2001), 42(8), 3437-3443.
Gao, C., "Preparation of Water Soluble hyperbranched poly(sulfone-amine)s by polyaddition of N-ethylethylenediamine to divinyl sulfone" Polymer (2001), 42(18), 7603-7610.
Gao, Chao, "Hyperbranched copolymers made from A2, B2 and BB'2 type monomers (iv). Copolymerization of divinyl sulfone with 4,4'-trimethylenedipiperidine and N-ethylethylenediamine" Science in China, Series B: Chemistry (2001), 44(2), 207-215.
Gao, Chao, "Hyperbranched copolymers made from A2, B2 and BB'2 type monomers, 3a: comparison of copoly(sulfone-amine)s containing piperazine and 4,4'-trimethylenedipiperidine units" Macromolecular Chemistry and Physics (2001), 202(15), 3035-3042.
Gao, Chao, "Hyperbranched polymers made from A2- and BB2'-type monomers; 3. Polyaddition of N-methyl 1,3-propanediamine to divinyl sulfone" Macromolecular Chemistry and Physics (2001), 202(12), 2623-2629.
Gao, Chao, "Polyaddition of B2 and BB'2 Type Monomers to A2 Type Monomer. 1. Synthesis of Highly Branched Copoly(sulfon-amine)s" Macromolecules (2001), 34(2), 156-161.
Gao, Chao, "Synthesis of hyperbranched polymers from commercially available A2 and BB'2 type monomers" Chemical Communications (Cambridge), 1 (2001) 107-108.
Hammouda, Y. et al. "The Use of Sodium Chloride as a Directly Compressible Filler in Therapeutic Tablets" Pharm. Ind., 37:5 (1975) 361-363.
Hobson, Lois J., et al. "Poly(amidoamine) Hyperbranched Systems:Synthesis, Structure and Characterization" Polymer, 40 (1999) 1279-1297.

Huval, Chad C. et al., "Syntheses of hydrophobically modified cationic hydrogels by copolymerization of alkyl substituted diallylamine monomers and their use as bile acid sequestrants" European Polymer Journal, 40 (2004) 693-701.
International Search Report dated Apr. 27, 2006 for PCT/US2005/039366.
Jansen, Johan F.G.A. et al. "The Dendritic Box: Shape-Selective Liberation of Encapsulated Guests" J. Am. Chem. Soc., 117 (1995) 4417-4418.
Janssen, H.M. et al, "The Synthesis and Characterization of Dendritic Molecules" Eindhoven University of Technology [No date available].
Jayamurugan, Govindasamy, et al., "Synthesis of Large Generation poly(propul ether imine) (PETIM) Dendrimers" Tetrahedron, 62 (2006) 9582-9588.
Katopodis, K. P. et al. "Effectiveness of Aluminum Hydroxide Timing Administration in Relation to Meals in Controlling Hyperphosphatemia in Dialysis Patients" The International Journal of Artificial Organs, 28:8 (2005) 803-807.
Klapper, Marcus et al., "Poly(methylene amine): A Polymer with the Maximum Possible Number of Amino Groups on a Polymer Backbone" Angew. Chem. Int. Ed., 42 (2003) 4687-4690 (XP002456407).
Koç, Fikret, et al. "Highly Regioselective Synthesis pf Amino-Functionalized Dendritic PolyGlycerols by a One Pot Hydroformylation/Reductive Amination Sequence" J. Org. Chem., 70 (2005) 2021-2025.
Kremer, Michael, et al., "Pore-Size Distributions of Cationic Polyacrylamide Hydrogels Varying in Initial Monomer Concentration and Crosslnker/Monomer Ratio" Macromolecules, 27 (1994) 2965-2973.
Kuga, Shigenori, "Pore Size Ditribution Analysis of Gel Substances by Size Exclusion Chromatography" J. Chromatography, 206 (1981) 449-461.
Lin, Shan-Yang et al. "Influence of Excipients, Drugs, and Osmotic Agent in the Inner Core on the Time-Controlled Disintegration of Compression-Coated Ethylcellulose Tablets" Journal of Pharmaceutical Sciences, 91:9 (Sep. 2002) 2040-2046.
Maroni, Bradley J. et al. "Renal Bioreplacement Therapy is Associated with a Reduction in Mortality in Patients with Acute Renal Failure: Results of a Randomized, Multi-Center, Phase II Trial" ERA-EDTA: Abstract #551794 (2006).
Mattsson, S. et al. "Formulation of High Tensile Strength Rapidly Disintegrating Tablets Evaluation of the Effect of Some Binder Properties" S.T.P. Pharma Sciences, 11:3 (2001) 211-220.
McGraw-Hill Dictionary of Scientific and Technical Terms, Third Ed., The Nikkan Kogyo Shimbu, Ltd., 1997, p. 54.
Mitchell, Karen et al. "The Influence of Additives on the Cloud Point, Disintegration and Dissolution of Hydroxypropylmethylcellulose Gels and Matrix Tablets" International Journal of Pharmaceutics, 66 (1990) 233-242.
Mourey, T. H., et al., "Unique Behavior of Dendritic Molecules: Intrinsic Viscosity of Polyether Dendrimers" Macromolecules, 25 (1992) 2401-2406.
Newkome, George R. et al., "Improved Synthesis of an Ethereal Tetraamine Core for Dendrimer Construction" J. Org. Chem., 67 (2002) 3957-3960.
Pavlov, G. M. et al. "Molecular Characteristics of Poly(propylene imine) Dendrimers as Studied with Translational Diffusion and Viscometry" Colloid. Polym. Sci., 280 (2002) 416-423.
Pérignon, Nelly et al., "Formation and Stabilization in Water of Metal Nanoparticles by a Hyperbranched Polymer Chemically Analgous to PAMAM Dendrimers" Chem Mater., 16 (2004) 4856-4858.
Physicians Desk Reference "Renagel", 2012.
"Renvela: sevelamer carbonate" Prescribing Information, Genzyme Corporation, Nov. 2007.
Rosenbaum, D.P, et al., "Effect of RenaGel, a non-absorbable, cross-linked, polymeric phosphate binder, on urinary phosphorus excretion in rats" Nephrology Dialysis Transplantation, vol. 12 (1997) 961-964.

(56) References Cited

OTHER PUBLICATIONS

Sarker, DiPak K. et al. "Restoration of Protein Foam Stability Through Electrostatic Propylene Glycol Alginate-Mediated Protein—Protein Interactions," Colloids and Surfaces B: Biointerfaces, 15 (1999) 203-213.

Schatzlein, Andreas G. et al., "Preferential liver gene expression with polypropylenimine dendrimers" Journal of Controlled Release, 101 (2005) 247-258.

Schulz, W. "Brief Evaluation: Sevelamer Hydrochloride" Drug, Therapy Criticism, Hans Marseille Publishers GmbH, Munich, Issue 3 (2001) 621-626.

Selmeczi, B. et al. "Investigations of the Influence of Some Novel Auxiliary Agents on the Physical Properties of Tablets" Pharmaceutical Technological Institute of the Medical University of Szeged (Hungary), [No date available].

Shao, Lu et al., "Transport properties of cross-linked polyimide membranes induced by different generations of diaminobutane (DAB) dendrimers" Journal of Membrane Science, 238 (2004) 153-163.

Soltero, Richard et al. "The Effects of PH. Ionic Concentration and Ionic Species of Dissolution Media on the Release Rates of Quinidine Gluconate Sustained Release Dosage Forms" Drug Development and Industrial Pharmacy, 17:1 (1991) 113-140.

Stasko, Nathan A. et al., "Dendrimers as a Scaffold for Nitric Oxide Release" J. Am. Chem. Soc., 128 (2006) 8265-8271.

Sugimoto, H., et al.; Journal of Food Processing and Preservations, 1981, 5:83-93.

Tirkkonen, Sirpa et al. "Enhancement of Drug Release from Ethylcellulose Microcapsules Using Solid Sodium Chloride in the Wall" International Journal of Pharmaceutics, 88 (1992) 39-51.

Tirkkonen, Sirpa et al. "Release of Indomethacin from Tabletted Ethylcellulose Microcapsules" International Journal of Pharmaceutics, 92 (1993) 55-62.

Written Opinion dated Apr. 27, 2006 for PCT/US2005/039366.

Xiao, Youchang et al., "Effects of Thermal Treatments and Dendrimers Chemical Structures on the Properties of Highly Surface Cross-Linked Polyimide Films" Ind. Eng. Chem. Res., 44 (2005) 3059-3067.

Xiuru Li, et al., "Synthesis and Characterization of Hyperbranched Poly(ester amide)s from Commercially Available Dicarboxylic Acids and Multihydroxyl Primary Amines" Macromolecules, 39 (2006) 7889-7899.

Yan, Deyue, "Hyperbranched Polymers made from A2 and BB'2 Type Monomers. 1. Polyaddition of 1-(2-Aminoethyl)piperazine to Divinyl Sulfone" Macromolecules (2000), 33(21), 7693-7699.

Zhuzhu, "New Drug to Decrease the Phosphorous in Blood—Sevelamer Hydrochloride", Chinese Pharmaceutical Journal, 1999, 34:7, 496-497 [English translation provided].

| Run No. | Actual Moisture Content (%LOD) | Stearic Acid (%) | Aerosil (%) | Lubricant Blend Time (min.) | Compression Force (kg) | Hardness (N) | Friability (%) | Disintegral Time (min) | Flow rate (g/sec.) | Thickness (inch x 1000) |
|---|---|---|---|---|---|---|---|---|---|---|
| 5 | 8.11 | 0.5 | 0.25 | 2 | 2000 | 228 | 0.25 | 6.58 | 0.619 | 306 |
| 7 | 8.139 | 0.25 | 0.5 | 2 | 2000 | 321 | 0.25 | 5.6 | 0.511 | 303 |
| 11 | 8.21 | 0.25 | 0.25 | 7 | 2000 | 248 | 0.12 | 5.24 | 0.619 | 305 |
| 17 | 7.998 | 0.5 | 0.5 | 7 | 2000 | 156 | 0.25 | 3.84 | 0.549 | 308 |
| 19 | 7.94 | 0.375 | 0.375 | 4.5 | 1750 | 181 | 0 | 2.31 | 0.582 | 309 |
| 3 | 8.328 | 0.25 | 0.25 | 2 | 1500 | 184 | 0 | 5.88 | 0.61 | 312 |
| 9 | 7.963 | 0.5 | 0.5 | 2 | 1500 | 149 | 0.25 | 5.12 | 0.495 | 312 |
| 13 | 8.098 | 0.5 | 0.25 | 7 | 1500 | 146 | 0.16 | 4.54 | 0.669 | 313 |
| 15 | 8.247 | 0.25 | 0.5 | 7 | 1500 | 149 | 0.31 | 5.17 | 0.543 | 316 |
| 27 | 6.576 | 0.375 | 0.375 | 4.5 | 2000 | 152 | 0.5 | 3.27 | 0.47 | 309 |
| 20 | 6.584 | 0.25 | 0.375 | 4.5 | 1750 | 170 | 0.38 | 3.12 | 0.503 | 313 |
| 22 | 6.509 | 0.375 | 0.25 | 4.5 | 1750 | 134 | 0.5 | 3.6 | 0.557 | 314 |
| 24 | 6.674 | 0.375 | 0.375 | 2 | 1750 | 167 | 1.25 | 3.24 | 0.525 | 313 |
| 1 | 6.718 | 0.375 | 0.375 | 4.5 | 1750 | 116 | 1.27 | 3.66 | 0.509 | 313 |
| 28 | 6.615 | 0.375 | 0.375 | 4.5 | 1750 | 129 | 0.88 | 2.6 | 0.514 | 315 |
| 29 | 6.555 | 0.375 | 0.375 | 4.5 | 1750 | 120 | 1.27 | 2.77 | 0.526 | 317 |
| 25 | 6.682 | 0.375 | 0.375 | 7 | 1750 | 106 | 1.76 | 6.39 | 0.519 | 315 |
| 23 | 6.509 | 0.375 | 0.5 | 4.5 | 1750 | 130 | 1.25 | 3.91 | 0.492 | 315 |
| 21 | 6.636 | 0.5 | 0.375 | 4.5 | 1750 | 111 | 1.87 | 3.37 | 0.513 | 317 |
| 26 | 6.54 | 0.375 | 0.375 | 4.5 | 1500 | 96 | 2.02 | 3.12 | 0.531 | 322 |
| 2 | 5.57 | 0.5 | 0.25 | 2 | 2000 | 181 | 0.25 | 4.22 | 0.478 | 311 |
| 8 | 5.079 | 0.5 | 0.5 | 2 | 2000 | 134 | 0.87 | 3.1 | 0.319 | 316 |
| 12 | 5.058 | 0.25 | 0.25 | 7 | 2000 | 85 | 3.25 | 2.25 | 0.474 | 319 |
| 14 | 4.914 | 0.25 | 0.5 | 7 | 2000 | 129 | 1.02 | 3.78 | 0.439 | 318 |
| 18 | 4.932 | 0.375 | 0.375 | 4.5 | 1750 | 104 | 2.01 | 2.85 | 0.406 | 322 |
| 4 | 5.034 | 0.5 | 0.25 | 2 | 1500 | 74 | 3.78 | 3.02 | 0.451 | 329 |
| 6 | 4.892 | 0.5 | 0.5 | 2 | 1500 | 128 | 1 | 3.67 | 0.366 | 328 |
| 10 | 5.211 | 0.25 | 0.25 | 7 | 1500 | 80 | 3.06 | 1.21 | 0.461 | 327 |
| 16 | 5.32 | 0.5 | 0.5 | 7 | 1500 | 45 | 5.99 | 1.03 | 0.384 | 331 |

DIRECT COMPRESSION POLYMER TABLET CORE

RELATED APPLICATIONS

This application is a continuation of U.S. application Ser. No. 13/467,448, filed May 9, 2012, which is a continuation of U.S. application Ser. No. 12/461,143, filed Aug. 3, 2009, now U.S. Pat. No. 8,187,631 issued on May 29, 2012, which is a continuation of U.S. application Ser. No. 11/196,799, filed Aug. 3, 2005, which is a further continuation of U.S. application Ser. No. 10/785,322, filed Feb. 24, 2004, which is a continuation of U.S. application Ser. No. 09/691,429, filed Oct. 18, 2000, now U.S. Pat. No. 6,733,780 issued on May 11, 2004, which claims the benefit of U.S. Provisional Application No. 60/160,258, filed Oct. 19, 1999, and U.S. Provisional Application No. 60/174,227, filed Jan. 3, 2000. The foregoing related applications, in their entirety, are incorporated herein by reference.

BACKGROUND OF THE INVENTION

A number of polymeric materials having useful therapeutic activity have been described for treatment of various conditions such as hyperlipidemia and hyperphosphatemia. Many of these polymeric materials function as non-absorbed ion exchange resins in the digestive tract. Such non-absorbed polymeric materials bind or otherwise sequester a target molecule and facilitate its removal from the body via the gastrointestinal tract. Examples of such resins include: Colestipol and Cholestyramine useful as orally administered cholesterol lowering agents; a variety of aliphatic amine polymers disclosed U.S. Pat. Nos. 5,496,545 and 5,667,775 useful as phosphate binders particularly for removing phosphate from patients suffering from renal failure; and other aliphatic amine polymers disclosed in U.S. Pat. No. 5,624,963, U.S. Pat. No. 5,679,717, WO98/29107 and WO99/22721 useful as cholesterol lowering agents.

Non-absorbed polymer therapeutics have traditionally presented a number of formulation challenges as the dosages are generally very large (gram quantities), and the resins tend to be extremely hydrophilic. The most desirable formulation for oral delivery of a therapeutic is a direct compression tablet formulation. However, not all therapeutics, particularly given the high dose requirements of polymeric ion exchange therapeutics, lend themselves to a tablet formulation. Even if such materials could be rendered into a tablet, it is generally not possible without the significant addition of other materials which assist in the tableting process. Ultimately the addition of any materials other than the active ingredient is undesirable given the dose requirement of the active ingredient. Ideally the tablet should contain as much active ingredient as possible with little else in the way of additional materials such that the tablet is as small as possible and easy to administer to the patient.

In addition, once the polymeric materials are compressed into a tablet, the tablet requires a coating for ease of administration to the patient. It has been discovered that the core polymeric material tends to be very hygroscopic, and thus will swell immediately upon contact with the inside of the mouth. Most coatings contain water, and thus it was believed that coating such tablets with a water-based coating would be impossible because the hygroscopic tablets would swell during the coating process. Thus providing a tablet core comprising a hygroscopic material such that a suitable coating may be used in conjunction with that core, is another significant challenge to providing the polymeric active ingredient in tablet form.

There is a need to provide suitable dosage forms for polymeric ion exchange materials, particularly for hydrophilic aliphatic amine polymers useful as therapeutic agents, which minimize the overall amount of material administered to the patient, which are easy to administer orally, and which are stable upon production and storage.

SUMMARY OF THE INVENTION

The present invention provides a tablet core which comprises at least about 95% by weight of an aliphatic amine polymer. In a preferred embodiment, the aliphatic amine polymer resin is a cross-linked polyallylamine resin. The aliphatic amine polymer is preferably hydrated. The hydrated polymer can, for example, comprise from about 5% water by weight or greater.

The invention also provides a method of producing a tablet core comprising at least about 95% by weight of an aliphatic amine polymer resin. The method comprises the step of compressing the aliphatic amine polymer to form the tablet core. The tablet core can further include one or more excipients. In this embodiment, the method of producing the tablet core comprises the steps of: (1) hydrating or drying the aliphatic amine polymer to the desired moisture level; (2) blending the aliphatic amine polymer with the excipients in amounts such that the polymer comprises at least about 95% by weight of the resulting blend; and (3) compressing the blend to form the tablet core. The present invention further relates to a coated tablet wherein the coating comprises a water based coating.

BRIEF DESCRIPTION OF THE DRAWINGS

The FIGURE is a table comprising data showing formulations and responses for sevelamer hydrochloride compressed tablet cores.

DETAILED DESCRIPTION OF THE INVENTION

A number of polymeric materials having useful therapeutic activity have been discussed above. In particular, aliphatic amine polymers have been disclosed which are useful in methods of lowering the serum phosphate level of a patient and lowering the serum cholesterol level of a patient. For example an epichorohydrin-cross-linked poly(allylamine hydrochloride) resin (U.S. Pat. Nos. 5,496,545 and 5,667,775), also referred to as sevelamer hydrochloride or sevelamer and marketed as RENAGEL®, has been shown to be effective at removing phosphate from human patients suffering from renal failure. Therapeutically effective dosages of sevelamer hydrochloride are large, typically on the order of 4 to 6 grams per day. Consequently, development of a dosage form of this and similar resins which minimizes the amount of excipient material is desirable.

The present invention provides a tablet core comprising at least about 95% by weight of an aliphatic amine polymer. The aliphatic amine polymer resin can be any of the aliphatic amine resins described in U.S. Pat. Nos. 5,496,545; 5,667,775; 5,624,963; 5,703,188; 5,679,717; 5,693,675; 5,607,669; 5,618,530; 5,487,888; and 5,702,696, each of which is hereby incorporated herein by reference in its entirety. Other suitable aliphatic amine polymers are disclosed in U.S. Ser. Nos. 08/670,764; 08/959,471, and 08/979,096, each of which is hereby incorporated by reference herein in its entirety. In a particularly preferred embodiment, the aliphatic amine polymer is polyallylamine, polyvinylamine, poly(diallylamine) or poly(ethyleneimine) or a salt thereof with a pharmaceutically acceptable acid. The aliphatic amine polymer is optionally substituted at one or more nitrogen atoms with an alkyl group or a substituted alkyl group such as a trialkylammonioalkyl group. The aliphatic amine polymer can optionally be cross-linked, for example via a multifunctional monomer or a bridging group which connects two amino nitrogen atoms from two different polymer strands. In a preferred embodiment, the aliphatic amine polymer resin is hydrated. For sevelamer hydrochloride, in particular, the compressibility is strongly dependent upon the degree of hydration (moisture content) of the resin. Preferably, the resin has a moisture content of about 5% by weight or greater, more preferably, the moisture content is from about 5% to about 9% by weight, and most preferably about 7% by weight. It is to be understood that in embodiments in which the polymer resin is hydrated, the water of hydration is considered to be a component of the resin. Thus, in this embodiment, the tablet core comprises at least about 95%, preferably at least about 96%, and more preferably at least about 98% by weight of the hydrated polymer, including the water of hydration.

The tablet can further comprise one or more excipients, such as hardeners, glidants and lubricants, which are well known in the art. Suitable excipients include colloidal silicon dioxide, stearic acid, magnesium silicate, calcium silicate, sucrose, calcium stearate, glyceryl behenate, magnesium stearate, talc, zinc stearate and sodium stearylfumarate. The excipients can represent from 0 to about 5% of the tablet core by weight.

The tablet core of the invention is prepared by a method comprising the steps of: (1) hydrating or drying the aliphatic amine polymer to the desired moisture level; (2) blending the aliphatic amine polymer with any excipients to be included in amounts such that the polymer comprises at least about 95% by weight of the resulting blend; and (3) compressing the blend using conventional tableting technology.

The invention also relates to a stable, swallowable coated tablet, particularly a tablet comprising a hydrophilic core, such as a tablet comprising an aliphatic amine polymer, as described above. In one embodiment, the coating composition comprises a cellulose derivative and a plasticizing agent. The cellulose derivative is, preferably, hydroxypropylmethylcellulose (HPMC). The cellulose derivative can be present as an aqueous solution. Suitable hydroxypropylmethylcellulose solutions include those containing HPMC low viscosity and/or HPMC high viscosity. Additional suitable cellulose derivatives include cellulose ethers useful in film coating formulations. The plasticizing agent can be, for example, an acetylated monoglyceride such as diacetylated monoglyceride. The coating composition can further include a pigment selected to provide a tablet coating of the desired color. For example, to produce a white coating, a white pigment can be selected, such as titanium dioxide.

In one embodiment, the coated tablet of the invention can be prepared by a method comprising the step of contacting a tablet core of the invention, as described above, with a coating solution comprising a solvent, at least one coating agent dissolved or suspended in the solvent and, optionally, one or more plasticizing agents. Preferably, the solvent is an aqueous solvent, such as water or an aqueous buffer, or a mixed aqueous/organic solvent. Preferred coating agents include cellulose derivatives, such as hydroxypropylmethylcellulose. Typically, the tablet core is contacted with the coating solution until the weight of the tablet core has increased by an amount ranging from about 4% to about 6%, indicating the deposition of a suitable coating on the tablet core to form a coated tablet.

In one preferred embodiment, the solids composition of the coating solution is:

| Material | % W/W |
|---|---|
| HPMC low viscosity Type 2910, cUSP | 38.5% |
| HPMCE high viscosity Type 2910, cUSP | 38.5% |
| diacetylated monoglyceride | 23.0% |

Tablets may be coated in a rotary pan coater as is known in the art or any other conventional coating apparatus such as a column coater or a continuous coater.

Astonishingly, it has been found that an aqueous coating dispersion is suitable as a coating solution for tablets comprising a hygroscopic, or water-swellable substance, such as an aliphatic amine polymer tablet. For example, the coating composition provides a strong, elastic and moisture-permeable coating without causing significant concomitant swelling of the tablet core during the coating process. In a preferred embodiment, the coating composition provides a tablet coating which withstands the swelling and contraction of sevelamer hydrochloride tablets during exposure to varying humidity levels and other known stability tests. Further, the coating composition can be used to coat other aliphatic amine polymer tablets without excessive uptake by the tablet core of water from the coating solution during the coating process.

The present invention also relates to the use of an aliphatic amine polymer as a disintegrant in a tablet. In general, in this embodiment the aliphatic amine polymer is not the active ingredient in the tablet, but is added to the tablet to enhance the rate of disintegration of the tablet following administration. This allows a more rapid release of the active agent or agents. The tablet will generally include the aliphatic amine polymer, one or more active ingredients, such as therapeutic agents (medicaments), and, optionally, one or more additional excipients.

The aliphatic amine polymer can be one of the aliphatic amine polymers disclosed above, such as polyethyleneimine, polyvinylamine, polyallylamine, polydiallylamine or any of the aliphatic amine polymers disclosed in U.S. Pat. Nos. 5,496,545 and 5,667,775 and U.S. Ser. No. 08/777,408 and 08/964,498, the teachings of each of which are incorporated herein by reference. In one embodiment, the aliphatic amine polymer is a cross-linked polyallylamine or a salt thereof with a pharmaceutically acceptable acid. Preferably, the aliphatic amine polymer is an epichlorohydrin-cross-linked polyallylamine or salt thereof with a pharmaceutically acceptable acid, such as sevelamer or sevelamer hydrochloride.

The tablet which includes an aliphatic amine as a disintegrant will, generally, include a sufficient amount of the aliphatic amine polymer to effectively enhance the rate of tablet disintegration under conditions of use. For example, if the tablet is an oral doseage form and it is desired that the tablet disintegrate in the stomach of the patient, the tablet should include a sufficient amount of the polymer to enhance the disintegration rate of the tablet under the conditions encountered in the stomach. The appropriate amount of the polymer to be included in the tablet can be determined by one skilled in the art using known methods. Typically, the polymer, the active ingredient or ingredients and any additional fillers or excipients are combined by mixing, and the resulting mixture is compressed to form a tablet using conventional methods. The tablet core formed in this way can then be coated, for example, as described above, or by other methods and other coating compositions which are known in the art and suitable for the intended use of the tablet.

In one embodiment, the tablet which includes an aliphatic amine polymer as a disintegrant is intended for administration in vivo, for example, to a patient, such as a human. Preferably, the tablet is intended to be administered orally. In this embodiment, the active ingredient or ingredients will be a therapeutic or diagnostic agent. The tablet can also be intended for use in vitro, for example, to deliver an active ingredient to an aqueous environment, such as a swimming pool.

The invention will now be described in detail by reference to the following examples.

EXAMPLES

Example 1

Preparation and Characterization of 400 mg and 800 mg Sevelamer Hydrochloride Direct Compression Tablet Cores Preparation of Tablet Cores 400 mg sevelamer hydrochloride tablet cores were prepared from a blend consisting of 5000.0 g sevelamer hydrochloride, 50.0 g colloidal silicon dioxide, NF (Aerosil 200) and 50.0 g stearic acid. The sevelamer hydrochloride was hydrated to moisture content of 6% by weight. The blend was prepared by passing the sevelamer hydrochloride and colloidal silicon dioxide through a #20 mesh screen, transferring the mixture to a 16 quart PK blender and blending for five minutes. The stearic acid was then passed through an oscillator equipped with a #30 mesh screen, transferred into the 16 quart PK blender and blended for five minutes with the sevelamer hydrochloride/colloidal silicon dioxide mixture. The resulting blend was discharged into a drum and weighed. The final blend was then compressed on a 16 station Manesty B3B at 4 tons pressure using 0.280"×0.620" punches to give tablet cores with an average weight of 434 mg. The resulting tablets consisted of 425 mg 6% hydrated sevelamer hydrochloride (equivalent to 400 mg anhydrous sevelamer hydrochloride), 4.25 mg colloidal silicon dioxide and 4.25 mg stearic acid.

800 mg sevelamer hydrochloride tablet cores were prepared from 19.0 kg sevelamer hydrochloride, 0.19 kg colloidal silicon dioxide, and 0.19 kg stearic acid. The sevelamer hydrochloride had a moisture content of 6% by weight. The blend was prepared by passing the sevelamer hydrochloride and colloidal silicon dioxide through a #20 mesh screen, transferring the mixture to a PK blender and blending for five minutes. The stearic acid was then passed through an oscillator equipped with a #30 mesh screen, transferred into the PK blender and blended for five minutes with the sevelamer hydrochloride/colloidal silicon dioxide mixture. The resulting blend was then discharged into a drum and weighed. The final blend was then compressed in on a 16 station Manesty B3B at 4 tons pressure using 0.3125"×0.750" punches to give tablets with an average weight of 866 mg. The resulting tablets consisted of 850 mg 6% hydrated sevelamer hydrochloride (equivalent to 800 mg anhydrous sevelamer hydrochloride), 8.0 mg colloidal silicon dioxide and 8.0 mg stearic acid.

Characterization of Tablet Cores

The tablets prepared as described above were white to off-white, oval shaped, compressed tablets. The variation of the tablets prepared from each blend with respect to weight, thickness, friability, hardness, disintegration time and density was assessed. Standard methods in the art were employed for each of the measurements. The results, (not shown), indicate that the hardness, friability, thickness, and disintegration behavior of the sevelamer hydrochloride tablets all met industry-standard criteria.

Example 2

Coating of Sevelamer Hydrochloride Tablet Cores

Compressed core tablets prepared as described in Example 1 were coated in a coating pan with an aqueous coating solution having a solids composition comprising:

| Material | % W/W |
| --- | --- |
| HPMC low viscosity Type 2910, cUSP | 38.5% |
| HPMCE high viscosity Type 2910, cUSP | 38.5% |
| diacetylated monoglyceride | 23.0% |

The coating solution was applied to the compressed cores until a weight gain of approximately 4 to 6% was achieved. Stability studies—controlled room temperature, accelerated conditions, freeze/thaw and photosensitivity—for the coated sevelamer hydrochloride tablets were conducted in accordance with those procedures known in the art and described in the following references: International Committee on Harmonization (ICH) guidance "Q1A-Stability Testing of New Drug Substances and Products" (June 1997); ICH "Q1B-Guidelines for the Photostability Testing of New Drug Substances and Products" (November 1996); and ICH guidance "Q1C-Stability Testing for New Dosage Forms" (November 1996. The results (not shown) indicate that the coated tablets all met industry standard criteria.

Example 3

Factors Affecting the Processing and Performance Characteristics of Compressed Tablets (Prior to Coating)

In order to maintain consistently acceptable compressed tablet on a per batch basis, a number of correlative tests were performed in order to determine which factors most strongly impact the quality and integrity of the tablets. Studies such as weight variation, tablet hardness, friability, thickness, disintegration time, among others are known to those skilled in the art and are described in the United States Pharmacopeia (U.S.P.). "Hardness" means the measure of the force (measured herein in Newtons) needed to fracture a tablet when such tablet is placed lengthwise on a Hardness Tester. "Friability" is the measure of the mechanical strength of the tablet needed to withstand the rolling action of a coating pan and packaging. It is measured using a friabiliator. "Thickness" is the measure of the height of the tablet using a micrometer. "Disintegration Time" is the time necessary for the tablet to break apart in an appropriate solution at 37° C. and is measured in minutes.

Attainment of appropriate hardness (150-170 N hardness range) and friability (no more than 0.8%) is important to the success of the formulation. Having tablets with high hardness and low friability is particularly important when the tablets are to be coated as is the case with sevelamer hydrochloride tablets.

The FIGURE provides a table listing several different sevelamer hydrochoride tablet core formulations that vary by a number of factors including (actual) moisture content, and compression force used, excipient content among other variations. The data in The FIGURE indicates that the most important factor affecting the processing and performance characteristics of compressed tablets is the moisture content. All formulations provided good flow with little weight variation throughout the entire range of compositions. In addition, disintegration times were less than 5 minutes across the range of compositions. Thus, it appears that moisture content and compression force provide the most appropriate factors on which to establish operating ranges for hardness and friability.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:
1. A tablet, comprising:
   i) a hydrophilic, compressed core consisting essentially of:
      a) at least 95 wt. % sevelamer hydrochloride; and
      b) one or more excipients, comprising stearic acid or colloidal silicon dioxide; and
   ii) a water-based coating, comprising hydroxypropylmethylcellulose or diacetylated monoglyceride.
2. The tablet of claim 1, wherein the sevelamer hydrochloride is hydrated.
3. The tablet of claim 1, wherein the sevelamer hydrochloride comprises a moisture content of about 5 wt. % or greater.
4. The tablet of claim 1, wherein the sevelamer hydrochloride has a moisture content of about 5 wt. % to about 9 wt. %.
5. The tablet of claim 1, wherein the water-based coating comprises hydroxypropylmethylcellulose and diacetylated monoglyceride.
6. The tablet of claim 1, wherein the hydrophilic, compressed core has a hardness of at least 150 N.
7. The tablet of claim 1, wherein the hydrophilic, compressed core has a hardness of 150-170 N.
8. The tablet of claim 1, wherein the hydrophilic, compressed core has a friability of no more than 0.8%.
9. The tablet of claim 1, wherein the largest dimension of the hydrophilic, compressed core is at least 0.3125 inches.
10. The tablet of claim 1, wherein the largest dimension of the hydrophilic, compressed core is at least 0.620 inches.
11. The tablet of claim 1, wherein the hydrophilic, compressed core is formed from a 0.3125 in×0.750 in punch.
12. The tablet of claim 1, wherein the tablet is useful in removing phosphate from a patient in need thereof.
13. The tablet of claim 1, wherein the hydrophilic, compressed core comprises 400 mg or 800 mg of the sevelamer hydrochloride on an anhydrous basis.
14. The tablet of claim 1, wherein the hydrophilic, compressed core comprises 400 mg of the sevelamer hydrochloride on an anhydrous basis.
15. The tablet of claim 1, wherein the hydrophilic, compressed core comprises 800 mg of the sevelamer hydrochloride on an anhydrous basis.
16. The tablet of claim 15, wherein the largest dimension of the hydrophilic, compressed core is 0.750 inches.
17. The tablet of claim 15, wherein the water-based coating comprises hydroxypropylmethylcellulose and diacetylated monoglyceride.
18. The tablet of claim 14, wherein the largest dimension of the hydrophilic, compressed core is 0.750 inches.
19. The tablet of claim 18, wherein the water-based coating comprises hydroxypropylmethylcellulose and diacetylated monoglyceride.
20. The tablet of claim 1, wherein the largest dimension of the hydrophilic, compressed core is 0.750 inches.

* * * * *